United States Patent [19]

Fonda et al.

[11] Patent Number: Plant 6,809

[45] Date of Patent: May 23, 1989

[54] ROSE PLANT NAMED WEOPOP

[75] Inventors: Henry Fonda, Los Angeles; Luis Desamero, Studio City, both of Calif.

[73] Assignee: Weeks Wholesale Rose Grower, Inc., Ontario, Calif.

[21] Appl. No.: 116,278

[22] Filed: Nov. 2, 1987

[51] Int. Cl.[4] ..... A01H 5/00

[52] U.S. Cl. ..... Plt./8

[58] Field of Search ..... Plt./8

*Primary Examiner*—Robert E. Bagwill

*Attorney, Agent, or Firm*—Vincent G. Gioia

[57] ABSTRACT

A new decorative white miniature rose which is a sport of the rose known as "Popcorn".

2 Drawing Sheets

The present invention relates to a new and distinct variety of rose plant of the miniature rose class, which was discovered and first asexually reproduced by the named inventors herein. The denomination of this new rose is "Weopop".

The new variety cv. Weopop may be distinguished from other presently available commercial rose cultivars by the following combination of characteristics: its abundant production of flower clusters which provide a nearly continuous display of color in the garden, its bushy full slightly pendulous habit, its sweet honey-like fragrance, its above-average disease resistance - in Canoga Park, Calif., and its clean white bloom color essentially as described and illustrated herein. Asexual reproduction by budding of the new variety as performed in San Bernardino County, Calif. shows that the foregoing and other distinguishing characteristics come true to form and are established and transmitted through succeeding propagations.

The accompanying photographs illustrate both the parent plant (positioned on the left side) and the new cultivar (positioned on the right side) in one photograph and the blossom features of the new cultivar in the other photograph. Throughout this specification, color names are values based upon the Colour Chart of The Royal Horticultural Society of London, England.

The new rose may be distinguished from its unpatented parent, "Popcorn" by the following combination of characteristics: significantly larger leaves, significantly larger flower size, and significantly larger overall habit essentially as described and illustrated herein. Flower size of the parent "Popcorn" is 1.5 to 2 cm. and flower size of the new variety is 2.5 to 3 cm.

Descriptive matter which follows pertains to roses of the new cultivar grown outdoors in September in San Bernardino County, Calif.

FLOWER

The new variety usually bears several flowers per stem. Flowers are borne in irregular pyramidal clusters on normal strength medium long stems for the class. Outdoors the plant blooms very abundantly and nearly continuously during the growing season. The flowers have a moderate sweet honey fragrance.

BUD

The peduncle is of average length for the class, of slender to average caliper, and usually erect. It is almost entirely smooth with few stipitate glands, and numerous fine hairs. Peduncle color is between Yellow-Green 144B and Yellow-Green 146C.

Before the calyx breaks, the bud is of small to medium size for the class, moderatedly short in length, and pointed to globular in shape. The surface of the bud bears numerous stipitate glands usually with slender foliaceous parts extending beyond the tip of the bud equal to ½ or more of its length. Bud color before sepals fall, is between Yellow-Green 144B and Yellow-Green 146C.

The inner surface of the sepals is lined with fine wooly tomentum; sepal margins are lined with few finely cut foliaceous parts and some stipitate glands and hairs.

As the first petal opens, the bud is moderately small to medium size for the class, somewhat short to medium length, and somewhat pointed to globular in form. The color of the outside and inside surfaces of the newly opened petals is near Yellow-White 158B. The bud does open up well and is not prevented from opening by wet, cold, hot, or dry weather.

BLOOM

When fully open, the bloom is somewhat small to medium size for the class, ranging from 2.5 to 3.0 cms. in diameter. Petalage is double with 25 to 28 petals and 1 to 4 petaloids arranged regularly. When partially open, the bloom form is moderately cupped to globular, and the petals are somewhat loosely cupped. When fully open, the bloom form is somewhat more flat to cupped and the petals are more flat to undulated.

PETALS

The petals are of moderately light substance and of medium thickness, with inside surfaces slightly satiny and outside surfaces slightly shiny to satiny. The outside petals are somewhat narrowly obovate in shape with apices somewhat rounded and usually slightly notched with one notch. The inside petals are somewhat narrowly obovate to oblanceolate in shape with apices usually slightly notched with one to two notches.

NEWLY OPENED FLOWER

The outside and inside surface of the outside, intermediate and inner petals is between Yellow-White 158D and White 155B.

The general color effect of the newly opened flower is between Yellow-White 158D and White 155B.

THREE DAY OLD FLOWER

The outside and inside surface of the outside and inner petals is between White 155B and White 155D.

The general color effect of the three day old flower is between White 155B and White 155D.

On the spent bloom, the petals usually drop off cleanly and are not particularly affected by cold, hot, wet, or dry weather.

In September, blooms on the bush growing in the garden generally last from two to three days. Cut roses grown outdoors are kept at normal indoor living temperatures generally last from two to three days.

MALE REPRODUCTIVE ORGANS

Stamens are few in number and are arranged irregularly about the pistil; several are mixed with petaloids. The filaments are of moderately short length, many without anthers. The anthers are moderately small for the class and all open approximately at the same time. Another color is near Yellow-Orange 21B when immature and near Yellow 13A at maturity. Pollen is somewhat sparse and near Yellow 13C in color.

FEMALE REPRODUCTIVE ORGANS

Pistils are few in number (approximately 14). The styles are somewhat uneven, very short in length, somewhat average caliper, and moderately bunched. Stigma color is near Green-Yellow 1C. Ovaries are usually all enclosed in the calyx.

Hips have not been observed on this variety.

FOLIAGE

The compound leaves are usually comprised of three to seven and sometimes nine or more leaflets and are borne abundantly. The leaves are moderately large for the class, distinctively larger than its parent "Popcorn", somewhat heavy to crisp in texture, and semi-glossy in finish. The leaflets are shaped moderately oval with somewhat acute to mucronate apices and somewhat acute bases. Their margins are usually simply serrate.

The upper surface of the mature leaf is between Green 137A and Yellow-Green 147A. The under surface of the mature leaf is between Green 138B and Yellow-Green 148B. The upper surface of the young leaf is between Yellow-Green 146A and Yellow-Green 147A. The under surface of the young leaf is near Yellow-Green 147B.

The rachis is somewhat light to average in caliper and moderately grooved with some stipitate glands and hairs on the edges of the upper side. The under side of the rachis is somewhat smooth with few stipitate glands and small prickles.

The stipules are of moderately long length with medium width moderately short points that usually turn out at an angle of more than 90 degrees.

The plant displays an above average degree of resistance to powdery mildew and rust as compared to other commercial varieties grown under comparable conditions.

GROWTH

The new plant has a large growth habit for a cultivar of this class and may achieve growth as much as twice the height of the parent plant. It displays very vigorous growth and the canes are of light to medium caliper for the class.

The major stems are new Yellow-Green 146D. They bear few large prickles which are moderately long for the class. The large prickles are hooked moderately downward with a somewhat long narrow base; prickle color is near Greyed-Orange 165B. The major stem bears no small prickles and no hairs.

The branches are between Yellow-Green 144A and Yellow-Green 147A. They bear few large prickles which are moderately long for the class. The large prickles are hooked moderately downward with a somewhat long narrow base; prickle color is near Greyed-Yellow 161B. The branches bear no small prickles and no hairs.

The new shoots are between Yellow-Green 144B and Yellow-Green 147C. They bear few large prickles which are moderately long for the class. The large prickles are hooked moderately downward with a somewhat long narrow base; prickle color is near Greyed-Orange 165B. The shoots bear no small prickles and no hairs.

We claim:

1. A new and distinct variety of rose plant of the miniature rose class, and all parts thereof, substantially as shown and described, which is a sport of the parent rose known as "Popcorn"; the plant being particularly characterized by white flowers larger in size than its parent attractively displayed on a vigorous plant with dark green foliage larger than its parent.

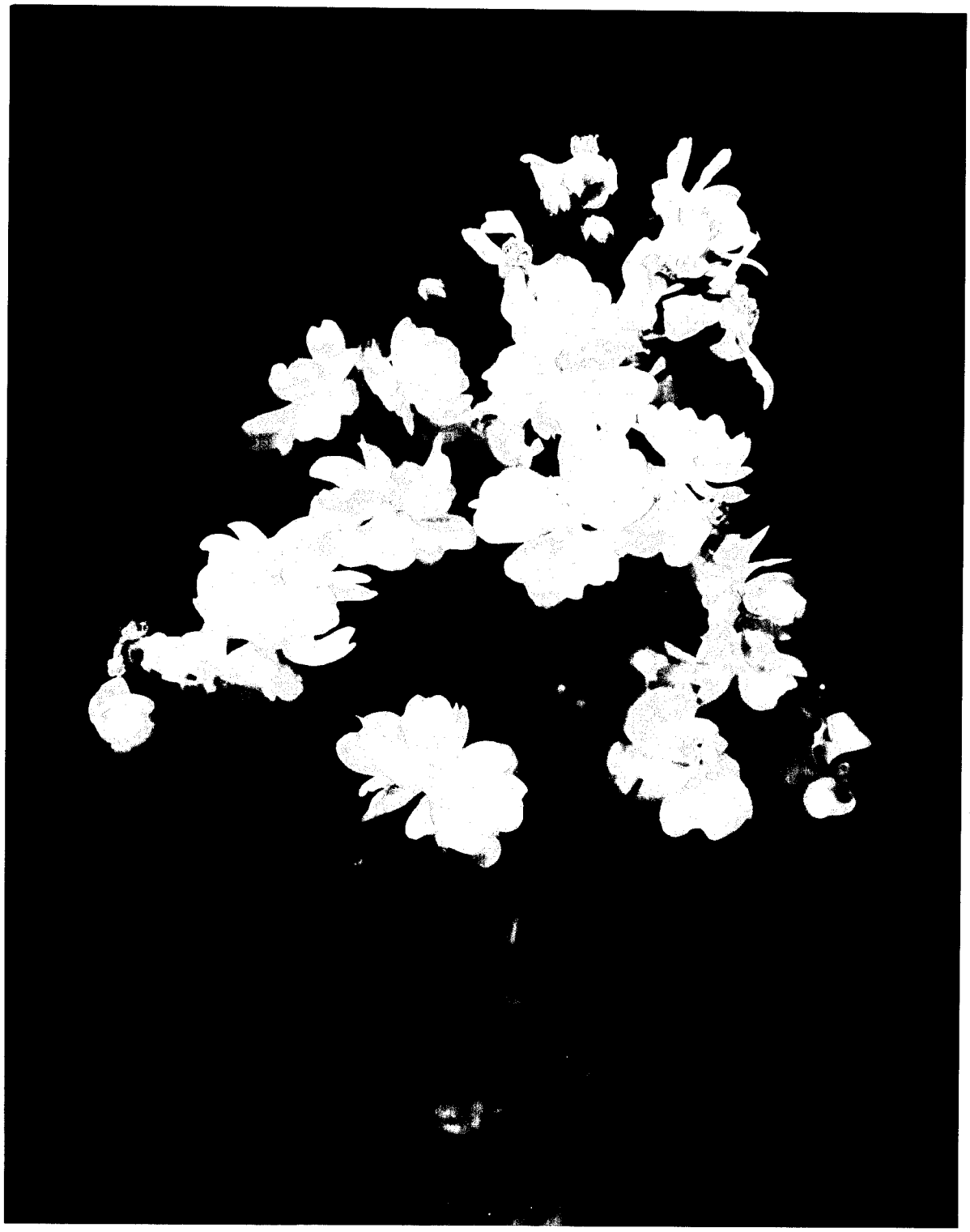

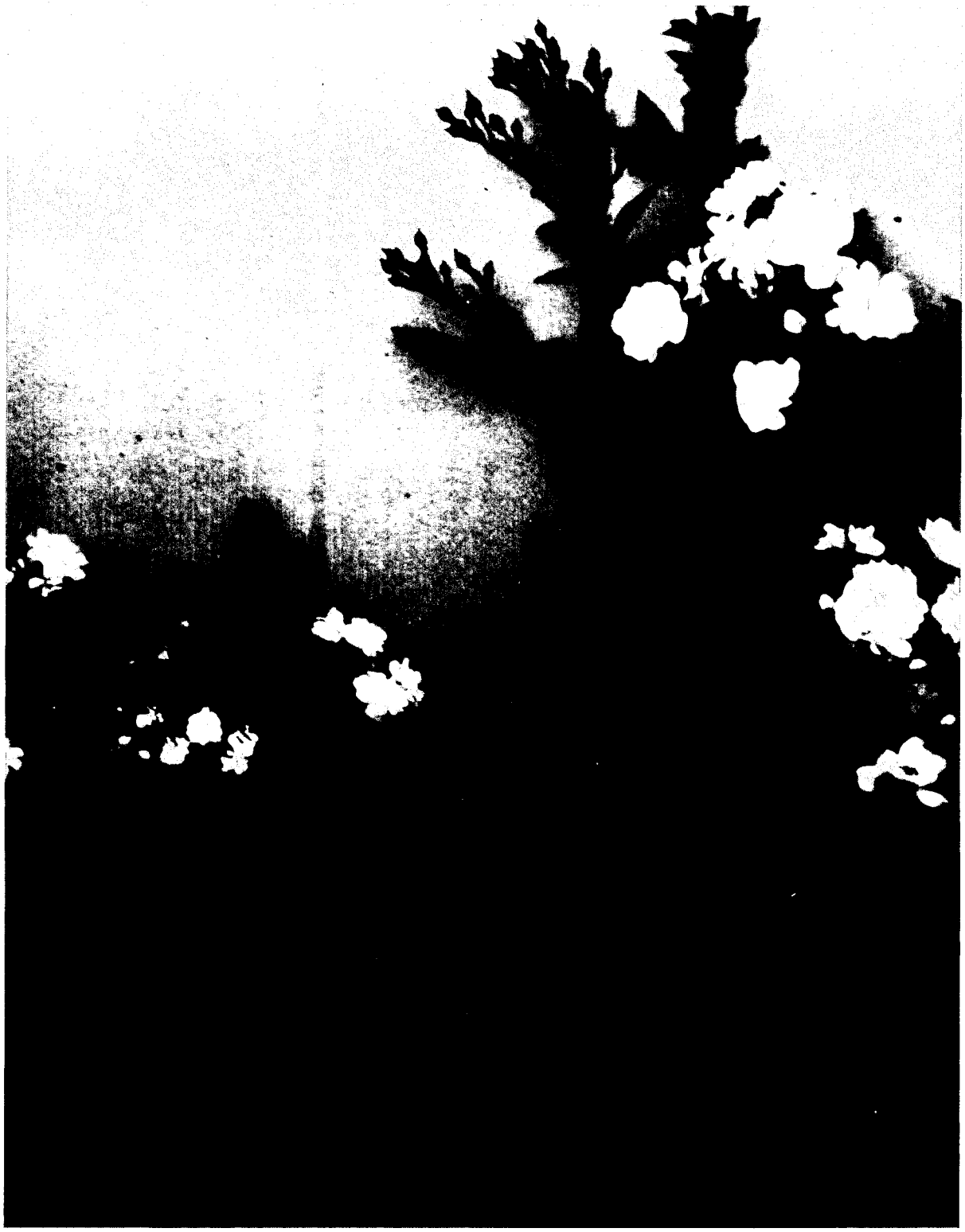

* * * * *